US011731955B2

(12) United States Patent
Dong et al.

(10) Patent No.: US 11,731,955 B2
(45) Date of Patent: Aug. 22, 2023

(54) CRYSTAL HABIT OF QUINOLINE DERIVATIVE AND PREPARATION METHOD FOR CRYSTALLINE POWDER THEREOF

(71) Applicant: CHIA TAI TIANQING PHARMACEUTICAL GROUP CO., LTD, Jiangsu (CN)

(72) Inventors: Ping Dong, Jiangsu (CN); Xiongxiong He, Jiangsu (CN); Lei Liu, Jiangsu (CN); Rui Zhao, Jiangsu (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 211 days.

(21) Appl. No.: 17/255,476

(22) PCT Filed: Jun. 24, 2019

(86) PCT No.: PCT/CN2019/092575
§ 371 (c)(1),
(2) Date: Dec. 23, 2020

(87) PCT Pub. No.: WO2020/001406
PCT Pub. Date: Jan. 2, 2020

(65) Prior Publication Data
US 2021/0276973 A1    Sep. 9, 2021

(30) Foreign Application Priority Data

Jun. 25, 2018 (CN) .......................... 201810662378.6

(51) Int. Cl.
| C07D 401/12 | (2006.01) |
| A61K 9/48 | (2006.01) |
| A61K 31/4709 | (2006.01) |
| A61P 35/00 | (2006.01) |

(52) U.S. Cl.
CPC ........ C07D 401/12 (2013.01); *C07B 2200/13* (2013.01)

(58) Field of Classification Search
CPC ............ C07D 401/12; C07B 2200/13; A61K 9/4866; A61K 31/4709; A61P 35/00
See application file for complete search history.

(56) References Cited

U.S. PATENT DOCUMENTS

| 8,148,532 B2 | 4/2012 | Chen |
| 9,751,859 B2 | 9/2017 | Chen et al. |
| 2016/0326138 A1* | 11/2016 | Chen .................... C07D 401/12 |

FOREIGN PATENT DOCUMENTS

| CN | 101809012 A | 8/2010 |
| CN | 102344438 A | 2/2012 |
| CN | 103664890 A | 3/2014 |
| CN | 103664892 A | 3/2014 |
| CN | 107771078 A | 3/2018 |
| WO | 2016/179123 A1 | 11/2016 |
| WO | WO 2018/112407 A1 | 6/2018 |

OTHER PUBLICATIONS

Loh, Z.H., et al. "Overview of milling techniques for improving the solubility of poorly water-soluble drugs." Asian Journal of Pharmaceutical Sciences, vol. 10, No. 4, Feb. 2015, pp. 255-274.
Zhong, C., et al. "Pharmacokinetics and disposition of anlotinib, an oral tyrosine kinase inhibitor, in experimental animal species." Acta Pharmacologica Sinica, vol. 39, No. 6, Apr. 2018, pp. 1048-1063.
Caira. "Crystalline Polymorphism of Organic Compounds". Topics in Current Chemistry, vol. 198, 1998, pp. 163-208.
Variankaval et al. "From Form to Function: Crystallization of Active Pharmaceutical Ingredients". American Institute of Chemical Engineers, vol. 54, No. 7, Jul. 2008, pp. 1682-1688.
Morissette et al. "High-throughput crystallization: polymorphs, salts, co-crystals and solvates of pharmaceutical solids". Advanced Drug Delivery Reviews, vol. 56, Issue 3, Feb. 2004, pp. 275-300.

* cited by examiner

*Primary Examiner* — John M Mauro
(74) *Attorney, Agent, or Firm* — Oliff PLC

(57) ABSTRACT

The present application relates to the field of pharmaceutical technology, specifically to the crystal habit and crystalline powder preparation of quinoline derivatives, and more specifically, to the crystal habit and crystalline powder preparation of anlotinib dihydrochloride. The compound of formula II disclosed herein is a crystalline powder with a flaky crystal habit having a specific surface area $\geq 10$ m$^2$/g and a particle-size distribution of $X_{50} \leq 50$ μm and/or $X_{90} \leq 500$ μm, such that a large specific surface area is provided without reducing the particle size of the drug by a physical method under the condition of a broad particle-size distribution, and the drug can rapidly dissolving. In addition to excellent dissolution property, the crystalline powder is also beneficial to industrial manufacturing, featuring simplified process and cost-efficiency.

18 Claims, 2 Drawing Sheets

CRYSTAL HABIT OF QUINOLINE DERIVATIVE AND PREPARATION METHOD FOR CRYSTALLINE POWDER THEREOF

TECHNICAL FIELD

The present application relates to the field of pharmaceutical technology, specifically to the crystal habit and crystalline powder preparation of quinoline derivatives, and more specifically, to the crystal habit and crystalline powder preparation of anlotinib dihydrochloride.

BACKGROUND

Tyrosine kinase is a group of enzymes which catalyze the phosphorylation of tyrosine residues in proteins. It plays an important role in intracellular signal transduction, takes part in adjustment, signaling and development of normal cells, and is closely related to proliferation, differentiation, migration and apoptosis of tumor cells. Many receptor tyrosine kinases are associated with tumorigenesis and can be classified into epidermal growth factor receptor (EGFR), platelet-derived growth factor receptor (PDGFR), vascular endothelial growth factor receptor (VEGFR), fibroblast growth factor receptor (FGFR) and the like according to the structure of extracellular domain. Anlotinib and preparation methods thereof were first disclosed in Example 24 of Patent No. WO2008112407, and its chemical name is 1-((4-(4-fluoro-2-methyl-1H-indol-5-yloxy)-6-methoxyquinolin-7-yloxy)methyl)cyclopropylamine and the structure shown in formula I:

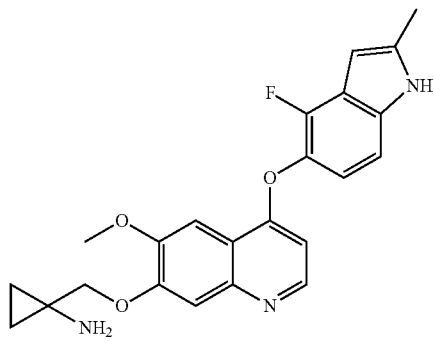

Formula I

Anlotinib dihydrochloride (the compound of formula II) is a compound prepared using the anlotinib and hydrochloric acid. It is a salt of a strong acid and a weak base and is generally present in the form of white or off-white powder or granules. Anlotinib dihydrochloride is easily absorbed in the acidic environment of stomach in human body, and demonstrates a reduced absorption rate and incomplete absorption in the alkaline environment of intestinal tract. Thus the preparation of the drug requires the characteristic of quick release.

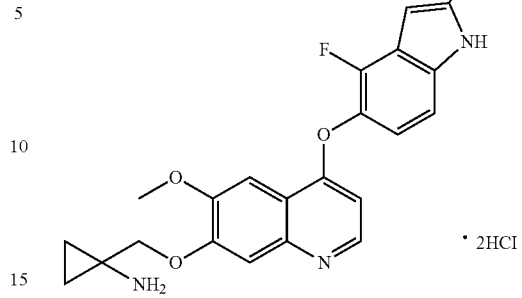

Formula II

Crystal habit generally refers to the overall external state of a crystal, and is a comprehensive presentation of the internal structure and physicochemical condition of formation of the crystal. For a substance, crystals formed in different crystallization conditions and solvent systems may have different basic crystal systems, as well as varied crystal habits. For example, a hexagonal crystal may have a stubby shape, elongated shape, or a shape of hexagonal flake or even polygonal needle. Crystal habit is one of the important considerations in the manufacture of crystal products. It greatly impacts not only the subsequent processes (such as filtration, washing, drying, and packaging) for the product, but also the particle-size distribution, specific surface area, bulk density, mechanical strength, fluidity, mixing characteristics, redissolving properties and the like of the final product, thereby influencing the storage, transportation and use of the product.

Therefore, to give an anlotinib dihydrochloride of specific crystal habit to facilitate its rapid dissolving is an objective of research and development for those skilled in the art.

SUMMARY

In a first aspect, the present application provides a crystalline powder of anlotinib dihydrochloride (the compound of formula II) having a crystal habit of a specific surface area $\geq 10$ m$^2$/g and a particle-size distribution $X_{50} \leq 50$ μm and/or $X_{90} \leq 500$ μm.

In some embodiments, the crystalline powder exhibits a flaky crystal habit. In some embodiments, the crystalline powder exhibits a thin flaky crystal habit. In some embodiments, the crystalline powder exhibits an aggregated flaky crystal habit. In some embodiments, the specific surface area is in the range of 10 to 50 m$^2$/g; in some embodiments, the specific surface area is in the range of 10 to 25 m$^2$/g; in some embodiments, the specific surface area is in the range of 10 to 15 m$^2$/g; in some embodiments, the specific surface area is in the range of 11 to 14 m$^2$/g; in some specific embodiments, the specific surface area is 11.1 m$^2$/g; in some specific embodiments, the specific surface area is 13.2 m$^2$/g. In some embodiments, the particle-size distribution is 20 μm$\leq X_{50} \leq$50 μm and/or 300 μm$\leq X_{90} \leq$500 μm; in some embodiments, the particle-size distribution is $X_{50} \leq$20 μm and/or 150 μm$\leq X_{90} \leq$300 μm; in some embodiments, the particle-size distribution is $X_{50} \leq$10 μm and/or 70 μm$\leq X_{90} \leq$150 μm; in some embodiments, the particle-size distribution is $X_{50} \leq$5 μm and/or 20 μm$\leq X_{90} \leq$70 μm; in some embodiments, the particle-size distribution is $X_{50} \leq$5 μm and/or $X_{90} \leq$20 μm; in some embodiments, the particle-size distribution is 1 μm$\leq X_{50} \leq$3 μm and/or $X_{90} \leq$15 μm.

In some embodiments, the specific surface area is in the range of 10 to 50 m²/g, and the particle-size distribution is 20 μm≤$X_{50}$≤50 μm and/or 300 μm≤$X_{90}$≤500 μm; in some embodiments, the specific surface area is in the range of 10 to 50 m²/g, and the particle-size distribution is $X_{50}$≤20 μm and/or 150 μm≤$X_{90}$≤300 μm; in some embodiments, the specific surface area is in the range of 10 to 25 m²/g, and the particle-size distribution is $X_{50}$≤10 μm and/or 70 μm≤$X_{90}$≤150 μm; in some embodiments, the specific surface area is in the range of 10 to 25 m²/g, and the particle-size distribution is $X_{50}$≤5 μm and/or 20 μm≤$X_{90}$≤70 μm; in some embodiments, the specific surface area is in the range of 10 to 15 m²/g, and the particle-size distribution is $X_{50}$≤5 μm and/or $X_{90}$≤20 μm; in some embodiments, the specific surface area is in the range of 10 to 15 m²/g, and the particle-size distribution is 1 μm≤$X_{50}$≤3 μm and/or $X_{90}$≤15 μm.

In some embodiments, the crystal includes, but is not limited to, the crystal forms of anlotinib dihydrochloride (the compound of formula II) described herein. In some embodiments, in the X-ray diffraction (XRD) pattern using Cu-Kα radiation, the crystal has diffraction peaks at the following 2θ of about 7.83, 8.83, 10.29, 14.63, 24.60 and 27.37; specifically, the crystal has diffraction peaks at the following 2θ of about 7.83, 8.83, 9.56, 10.29, 13.90, 14.63, 19.40, 20.19, 22.35, 22.91, 24.60 and 27.37; more specifically, the crystal has diffraction peaks at the following 2θ of about 7.83, 8.83, 9.56, 10.29, 13.90, 14.63, 15.34, 15.93, 17.32, 18.70, 19.40, 20.19, 22.35, 22.91, 24.60, 25.64, 27.37, 28.17 and 29.94.

In some embodiments, the crystalline powder has the characteristic of rapid dissolving, i.e., the crystalline powder has a dissolution of about 90% at 5 minutes in 0.1 mol/L hydrochloric acid and a standard medium of 10 mM phosphate buffer containing 0.075% SDS, pH 6.8 by basket dissolution method.

In a second aspect, the present application provides a crystalline powder of anlotinib dihydrochloride (the compound of formula II) with a flaky crystal habit having a specific surface area ≥10 m²/g and a particle-size distribution of $X_{50}$≤50 μm and/or $X_{90}$≤500 μm, wherein, in the XRD pattern using Cu-Kα radiation, the crystal has diffraction peaks at the following 2θ of about 7.83, 8.83, 10.29, 14.63, 24.60 and 27.37.

Specifically, the crystal has diffraction peaks at the following 2θ of about 7.83, 8.83, 9.56, 10.29, 13.90, 14.63, 19.40, 20.19, 22.35, 22.91, 24.60 and 27.37.

More specifically, the crystal has diffraction peaks at the following 2θ of about 7.83, 8.83, 9.56, 10.29, 13.90, 14.63, 15.34, 15.93, 17.32, 18.70, 19.40, 20.19, 22.35, 22.91, 24.60, 25.64, 27.37, 28.17 and 29.94.

In some embodiments, the crystal exhibits a thin flaky crystal habit. In some embodiments, the crystal exhibits an aggregated flaky crystal habit. In some embodiments, the specific surface area is in the range of 10 to 50 m²/g; in some embodiments, the specific surface area is in the range of 10 to 25 m²/g; in some embodiments, the specific surface area is in the range of 10 to 15 m²/g; in some embodiments, the specific surface area is in the range of 11 to 14 m²/g; in some specific embodiments, the specific surface area is 11.1 m²/g; in some specific embodiments, the specific surface area is 13.2 m²/g. In some embodiments, the particle-size distribution is 20 μm≤$X_{50}$≤50 μm and/or 300 μm≤$X_{90}$≤500 μm; in some embodiments, the particle-size distribution is $X_{50}$≤20 μm and/or 150 μm≤$X_{90}$≤300 μm; in some embodiments, the particle-size distribution is $X_{50}$≤10 μm and/or 70 μm≤$X_{90}$≤150 μm; in some embodiments, the particle-size distribution is $X_{50}$≤5 μm and/or 20 μm≤$X_{90}$≤70 μm; in some embodiments, the particle-size distribution is $X_{50}$≤5 μm and/or $X_{90}$≤20 μm; in some embodiments, the particle-size distribution is 1 μm≤$X_{50}$≤3 μm and/or $X_{90}$≤15 μm.

In some embodiments, the specific surface area is in the range of 10 to 50 m²/g, and the particle-size distribution is 20 μm≤$X_{50}$≤50 μm and/or 300 μm≤$X_{90}$≤500 μm; in some embodiments, the specific surface area is in the range of 10 to 50 m²/g, and the particle-size distribution is $X_{50}$≤20 μm and/or 150 μm≤$X_{90}$≤300 μm; in some embodiments, the specific surface area is in the range of 10 to 25 m²/g, and the particle-size distribution is $X_{50}$≤10 μm and/or 70 μm≤$X_{90}$≤150 μm; in some embodiments, the specific surface area is in the range of 10 to 25 m²/g, and the particle-size distribution is $X_{50}$≤5 μm and/or 20 μm≤$X_{90}$≤70 μm; in some embodiments, the specific surface area is in the range of 10 to 15 m²/g, and the particle-size distribution is $X_{50}$≤5 μm and/or $X_{90}$≤20 μm; in some embodiments, the specific surface area is in the range of 10 to 15 m²/g, and the particle-size distribution is 1 μm≤$X_{50}$≤3 μm and/or $X_{90}$≤15 μm.

In some embodiments, the crystalline powder has the characteristic of rapid dissolving, i.e., the crystalline powder has a dissolution of about 90% at 5 minutes in 0.1 mol/L hydrochloric acid and a standard medium of 10 mM phosphate buffer containing 0.075% SDS, pH 6.8 by basket dissolution method.

In one specific embodiment, using Cu-Kα radiation, a typical XRD pattern of the crystal is shown in FIG. 1, which has the following characteristics:

| Serial number | 2θ (°) | d value (Å) | Relative strength (%) |
|---|---|---|---|
| 1 | 7.83 | 11.28 | 29.0 |
| 2 | 8.83 | 10.01 | 23.5 |
| 3 | 9.56 | 9.25 | 9.2 |
| 4 | 10.29 | 8.59 | 79.6 |
| 5 | 13.90 | 6.37 | 14.3 |
| 6 | 14.63 | 6.05 | 63.0 |
| 7 | 15.34 | 5.77 | 12.7 |
| 8 | 15.93 | 5.56 | 11.6 |
| 9 | 16.13 | 5.49 | 5.3 |
| 10 | 17.32 | 5.11 | 7.4 |
| 11 | 18.70 | 4.74 | 17.9 |
| 12 | 19.40 | 4.57 | 28.5 |
| 13 | 19.79 | 4.48 | 14.8 |
| 14 | 20.19 | 4.39 | 28.8 |
| 15 | 21.42 | 4.14 | 9.4 |
| 16 | 21.92 | 4.05 | 13.6 |
| 17 | 22.35 | 3.97 | 27.7 |
| 18 | 22.91 | 3.88 | 23.3 |
| 19 | 23.53 | 3.78 | 11.4 |
| 20 | 24.60 | 3.62 | 100.0 |
| 21 | 25.36 | 3.51 | 14.4 |
| 22 | 25.64 | 3.47 | 18.5 |
| 23 | 25.92 | 3.43 | 11.8 |
| 24 | 26.85 | 3.32 | 11.3 |
| 25 | 27.37 | 3.26 | 34.1 |
| 26 | 28.17 | 3.16 | 13.8 |
| 27 | 28.85 | 3.09 | 8.7 |
| 28 | 29.47 | 3.03 | 7.9 |
| 29 | 29.94 | 2.98 | 24.0 |
| 30 | 30.69 | 2.91 | 11.8 |

In a third aspect, the present application provides a method for preparing an anlotinib dihydrochloride (the compound of formula II) crystalline powder of the aforementioned crystal habit, comprising:

(1) stirring, mixing and separating the compound of formula II and one or more slightly or hardly soluble organic solvents until no liquid flows out to give a mixture;

(2) heating and drying under reduced pressure to give the crystalline powder; and (3) optionally, pulverizing and mixing to give the crystalline powder.

The operation process of stirring, mixing and separating is also referred to as slurrying.

In step (1), the slightly or hardly soluble solvent is a slightly or hardly soluble solvent relative to the compound of formula II, wherein slightly soluble refers to that the solubility (20° C.) of the compound of formula II in the solvent is not less than 0.01 g and less than 1 g; hardly soluble refers to that the solubility of compound of formula II in the solvent (20° C.) is less than 0.01 g. In some embodiments, the slightly or hardly soluble organic solvent includes, but is not limited to, one or any mixture of ethanol, ethyl acetate, methanol, and acetone. In some embodiments, the organic solvent is ethanol; in some embodiments, the organic solvent is ethyl acetate; in some embodiments, the organic solvent is a mixture of ethyl acetate and ethanol; in some embodiments, more than one slightly or hardly soluble organic solvents are slurried in a certain order; in a specific embodiment, the compound of formula II is slurried sequentially with ethyl acetate and anhydrous ethanol.

In some embodiments, the mass ratio (m/m) of the compound of formula II to the solvent is from 1:4 to 1:10, preferably from 1:5 to 1:9. In a specific embodiment, the mass ratio (m/m) of the compound of formula II to ethyl acetate is 1:6 to 1:8; in a specific embodiment, the mass ratio (m/m) of the compound of formula II to ethyl acetate is 1:7. In a specific embodiment, the mass ratio (m/m) of the compound of formula II to anhydrous ethanol is 1:6 to 1:7; in a specific embodiment, the mass ratio (m/m) of the compound of formula II to anhydrous ethanol is 1:6.3. In some embodiments, the mixture may be separated by centrifugal filtration such that no liquid flows out. In a specific embodiment, the mixture is separated by centrifugal filtration, and the period of centrifugal filtration is generally 10 to 60 minutes, preferably 30 minutes.

In some embodiments, the means of heating in step (2) is water bath. In some embodiments, the water bath is at 20 to 40° C., preferably 25 to 35° C. In some embodiments, the vacuum degree of reduced-pressure drying is −0.2 to 0.2 MPa, preferably −0.10 to 0.06 MPa. In some embodiments, the completion of drying is assessed by measuring percent loss on drying. In some embodiments, drying is completed when the percent loss on drying reaches ≤1.5%. In some embodiments, the period of drying is generally 18 to 40 hours, preferably 24 to 30 hours.

In some embodiments, optionally, in step (3) a crystalline powder with smaller particle size is given by means of pulverization, and the pulverization technique includes, but is not limited to, mechanical pulverization, jet milling, ultrasonic pulverization, electromagnetic pulverization, and lyophilization ultrafine powder technique. In some embodiments, the crystalline powder is given by mechanical pulverization. In some embodiments, the crystalline powder is given by jet milling.

In a fourth aspect, the present application provides a crystalline powder composition having the aforementioned crystal habit. The crystalline powder composition represented by crystalline powder having the flaky crystal habit accounts for 50 wt % or more, preferably 70 wt % or more, more preferably 90 wt % or more, and most preferably 95 wt % or more by weight of the crystalline powder composition of anlotinib dihydrochloride (the compound of formula II). The composition may comprise a small amount of the compound of formula II in other crystal forms or amorphous forms. The anlotinib dihydrochloride (the compound of formula II) crystalline powder of flaky crystal habit and its pharmaceutical composition are hereinafter referred to as "active substance of the present application".

The active substance of the present application may be administered by any route suitable for the target conditions, including oral, topical (e.g., buccal, sublingual, etc.), parenteral (e.g., subcutaneous, intramuscular, intravenous, intraspinal, intradermal, intrathecal, etc.), rectal, vaginal, and other routes. The preferred route of administration is oral administration.

Although the active substance of the present application can be administered in the form of a pure substance, they are generally administered in the form of a pharmaceutical composition. The pharmaceutical composition containing the active substance of the present application also comprises one or more pharmaceutically acceptable carriers, diluents or excipients, and optionally, other therapeutically active ingredients.

Pharmaceutical compositions suitable for parenteral administration include injection forms such as sterile solutions, suspensions or emulsions, preferably a sterile solution. Pharmaceutical compositions suitable for oral administration include tablets, capsules, powders, granules, dripping pills, pastes, pulvis, tinctures, sustained release agents, solutions, suspensions and the like, preferably a tablet and capsule. The tablet may be a common tablet, dispersible tablet, effervescent tablet, sustained-release tablet, controlled-release tablet or enteric coated tablet. The capsule may be a common capsule, sustained-release capsule, controlled-release capsule or enteric coated capsule. The pharmaceutical composition of the present application can be prepared by a conventional method using a conventional pharmaceutical excipient known in the art. Conventional pharmaceutic excipients include fillers, absorbents, wetting agents, binders, disintegrants, lubricants, carriers, diluents, isoosmotic adjusting agents, acidity regulator and the like. The fillers include starch, lactose, mannitol, microcrystalline cellulose, pregelatinized starch, glucose, and the like; the absorbents include calcium sulfate, calcium hydrophosphate, calcium carbonate, magnesium oxide, and the like; wetting agents include water, ethanol, and the like; the binders include cellulose derivatives (such as hydroxypropyl methylcellulose, methylcellulose, sodium hydroxymethyl cellulose, and ethyl cellulose), polyvidone, microcrystalline cellulose, sodium alginate, polyethylene glycol, magnesium aluminum silicate, starch slurry, dextrin, powder sugar, syrup, and the like; the disintegrants include croscarmellose sodium, crospovidone, dry starch, low-substituted hydroxypropyl cellulose, sodium carboxymethyl starch, polysorbate 80, sodium alginate, and the like; the lubricants include magnesium stearate, stearic acid, polyethylene glycol, magnesium dodecyl sulfate, sodium dodecyl sulfate, silica gel micropowder, talcum powder, hydrogenated castor oil, glyceryl behenate, and the like; the carrier is selected from the group consisting of lactose, mannitol, trehalose, glycine, and the like; the diluent is selected from the group consisting of aqueous vehicles such as distilled water and/or sterile water for injection, bacteriostatic water for injection optionally containing methylparaben and/or propylparaben and/or 0.9% benzyl alcohol, normal saline such as 0.9% sodium chloride solution or 0.45% or 0.225% sodium chloride solution, Ringer's solution and/or Ringer's lactate solution, and the like; the isoosmotic adjusting agent is selected from the group consisting of glucose, sodium chloride, potassium chloride, mannitol, and the like; the acidity regulator is selected from the group consisting of sodium hydroxide, ammonium hydroxide, hydrochloric acid, sodium carbonate, sodium bicarbonate, dilute sulfuric acid, citric acid, sodium citrate, acetic acid, tartaric acid, sodium acetate, disodium hydrogen phosphate, and the like; the pharmaceutical excipients further include coloring agents, sweeteners and the like. The sweetener is selected from the group consisting of stevioside, aspartame, and the like. The coloring agent is selected from the group consisting of titanium dioxide, iron oxide red, iron oxide yellow, and the like.

The present application provides a method for treating non-small cell lung cancer comprising administering to a non-small cell lung cancer patient a therapeutically effective amount of an active substance of the present application or a pharmaceutical composition thereof. In some embodiments, the method comprises administering to a non-small cell lung cancer patient a therapeutically effective amount of an active substance of the present application.

In another aspect, the present application provides a kit comprising an active substance of the present application and a pharmaceutical composition thereof, a package insert and a suitable package. In some embodiments, the disclosure relates to a method for treating non-small cell lung cancer, comprising administering to a non-small cell lung cancer patient a therapeutically effective amount of an active substance of the present application.

It should be noted that the crystal habit described herein refers to a habit of crystal exhibited in the external shape of a crystal. The flaky crystal habit described herein refers to a crystal habit that the crystal structure develops in a horizontal direction and the crystal exhibits a thin flaky or a platelet-shaped characteristic. The flaky crystal habit features a specific surface area ≥10 m$^2$/g and a particle-size distribution of $X_{50}$≤50 μm and/or $X_{90}$≤500 In some embodiments, a crystalline powder of such flaky crystal habit exhibits a thin flaky shape; in some embodiments, a crystalline powder of such flaky crystal habit exhibits an aggregated flaky shape. The thin flaky crystalline powder can form the crystalline powder of the aggregated flaky shape through interaction.

In the present application, the diffraction pattern acquired from a crystal compound, described herein in the X-ray diffraction (XRD) pattern, is generally characteristic for a particular crystal, where the relative intensities of the bands may vary due to dominant orientation effects arising from differences in crystallization conditions, particle size, and other measurement conditions. Therefore, the relative intensities of the diffraction peaks are not characteristic for the crystal concerned, and it is important to consider the relative positions of the peaks rather than their relative intensities for determining whether it is the same as a known crystal. In addition, there may be slight errors in the position of the peaks for any given crystal, as is also well known in the field of crystallography. For example, the position of the peak may shift due to temperature changes, sample movement or calibration of the instrument when analyzing a sample and the error in the determination of 2θ value is typically ±0.2°. Therefore, this error should be considered when determining a crystal structure. In XRD pattern, the peak position is usually represented by 2θ angle or interplanar distance d, which has a simple conversion relationship: d=λ/2 sin θ, wherein d represents the interplanar distance, λ represents the wavelength of the incident X-ray, and θ is the diffraction angle.

"$X_{10}$" as used herein refers to the particle size for 10% of the particles in the particle size distribution, i.e., the fraction of particles smaller than this particle size accounts for 10% of all particles; "$X_{50}$" refers to the particle size for 50% of the particles in the particle size distribution, i.e., the fraction of particles smaller than this particle size accounts for 50% of all particles; "$X_{90}$" refers to a particle size for 90% of the particles in the particle size distribution, i.e., the fraction of particles smaller than this particle size accounts for 90% of all particles.

In the present application, the specific surface area A used herein refers to the total area per unit mass (m$^2$/g), as determined by multipoint BET specific surface area measurement.

For hardly soluble drugs, it is generally believed that the smaller the particle size of the drug, the faster the dissolution rate, as derived from the classical Noyes-Whitney equation:

$$\frac{dC}{dt} = kA(C_s - C)$$

wherein C is the concentration of dissolved drug; t is time; k is the dissolution rate constant of the drug; A is the specific surface area of the drug; and $C_s$ is the saturation concentration of the drug. When the test reaches the sink condition, the saturation concentration $C_s$ of the drug is much larger than the concentration C of the dissolved drug, at which point the Noyes-Whitney formula can be simplified as:

$$\frac{dC}{dt} = kAC_s$$

For a certain drug, the dissolution rate constant k and the saturation concentration Cs are both fixed values, and in this case, the dissolution rate dC/dt is positively correlated only with the specific surface area A of the drug. In general, it is believed that there is a certain correlation between the specific surface area A and the particle size r of a drug. For example, the inhalation lactose of DFE Pharma with a cubic block crystal habit, through measurement, gives a relationship between the particle size and the specific surface area as shown in table 1.

TABLE 1

Relationship between particle size and specific surface area of lactose

| Sample | $X_{10}$ (μm) | $X_{50}$ (μm) | $X_{90}$ (μm) | A (m$^2$/g) |
|---|---|---|---|---|
| Lactohale ®100 | 45-65 | 125-145 | 200-250 | 0.1 |
| Lactohale ®200 | 5-15 | 50-100 | 120-160 | 0.3 |
| Lactohale ®201 | 3-6 | 20-25 | 50-60 | 0.7 |
| Lactohale ®300 |  | <5 | <10 | 4.3 |

From the above table, it can be seen that when the shape and internal structure of the crystal are regular and simple, the specific surface area increases as the particle size decreases, demonstrating an inverse proportional relationship:

$$A \propto \frac{1}{r}.$$

Therefore, the particle size or specific surface area of the drug can be used as a parameter (as the following relation) to indirectly reflect the dissolution rate, thereby guiding the dissolution test:

$$\frac{dC}{dt} \propto A \propto \frac{1}{r}$$

Accordingly, in order to acquire a pharmaceutical preparation with a faster dissolution rate, those skilled in the art generally reduce the particle size of the drug by physical methods such as pulverization and micronization to provide a larger specific surface area, thereby increasing the dissolution rate.

For hardly soluble anlotinib dihydrochloride, referring to the preparation by recrystallization in ethanol disclosed in Patent No. CN107771078, bulk crystal was acquired, and in the process of preparing drug substance and product, it was found that the powder acquired from the bulk crystal of anlotinib dihydrochloride has strong cohesiveness. The powder after pulverization rapidly aggregates into lumps with different sizes and different degrees of tightness, and the cohesiveness is significantly enhanced along with the reduction of the particle size of the powder, so that the agglomeration phenomenon is more serious. This phenomenon results in poor mixing homogeneity of the drug substance during formulation. The strength of commercially available anlotinib capsules varies from 8 mg to 12 mg. For an anti-tumor drug with certain toxic and side effects, the accuracy and precision of the loading amount in a single preparation is extremely important.

Thus, there are two difficulties with preparing the bulk crystal of anlotinib dihydrochloride substance in the prior art. In one aspect, in order to accelerate dissolution, it is necessary to pulverize the drug substance to increase the specific surface area of substance particles. In another aspect, in the pulverization process, along with the reduction of the particle size of the powder and the increase of the specific surface area, the cohesiveness of the powder is obviously enhanced. The powder aggregates into lumps, reducing the mixing homogeneity and resulting in heterogeneous loading amount.

The anlotinib dihydrochloride (the compound of formula II) disclosed herein has a flaky (or aggregated flaky) crystal habit, and the particle-size distribution and the specific surface area of the crystalline powder are not in an inverse proportional relationship, such that a large specific surface area can be provided without excessively reducing the particle size of the drug by a physical method under the condition of a broader particle-size distribution, and the drug can rapidly dissolving. Meanwhile, in the particle-size distribution range, the cohesiveness of the anlotinib dihydrochloride is well controlled, resulting in good mixing homogeneity and advantages for preparation. Therefore, the crystalline powder disclosed herein and the pharmaceutical preparation thereof, such as an oral capsule, have excellent dissolution property and good mixing homogeneity, and are more beneficial to industrial manufacturing, featuring simplified process and cost-efficiency.

DETAILED DESCRIPTION

The technical solutions of the present application will be described with specific examples, but the scope of the present application is not limited to the scope of the following examples. The reagents used are all commercially available products.

The instrument and method for data acquisition:

X-ray powder diffraction (XRD) spectroscopy was performed under the following conditions: instrument: D/Max-RA RigakuXMiniFlex II X-ray powder diffractometer; ray: monochromatic Cu-Kα rays (λ=1.5418 Å); scanning mode: θ/2θ, scan range: 0-40°, voltage: 30 kV, current: 15 mA; detecting condition: temperature: 23.9° C., humidity: 38.6%.

The particle-size distribution of the materials was determined by laser. Instrument: fully automatic dry and wet two-in-one laser particle size analyzer, VIBRI (HELOSBR).

The specific surface area was determined by multipoint BET specific surface area measurement, in which the absolute adsorption quantity of nitrogen in a sample was measured under different partial pressures, and the single-layer adsorption quantity was calculated by the BET theory, thus giving the specific surface area.

Comparative Example 1. Preparation of Crystal of Compound of Formula II

About 126 mg of the compound of formula II, with reference to the method disclosed in Example 5 of Patent No. CN107771078, was added with 63 g of ethanol, dissolved and recrystallized in ethanol to obtain a bulk crystalline of the compound of formula II.

Because the compound of formula II was crystallized to form a bulk crystal with a large particle size, and the test range of the laser particle size analyzer is 0.1-500 μm, the particle size and distribution could not be measured by the laser particle size analyzer or a laser method.

The specific surface area of the bulk crystal of the compound of the formula II was determined by multipoint BET specific surface area measurement, which was 3.4750 m²/g.

Figure 1:
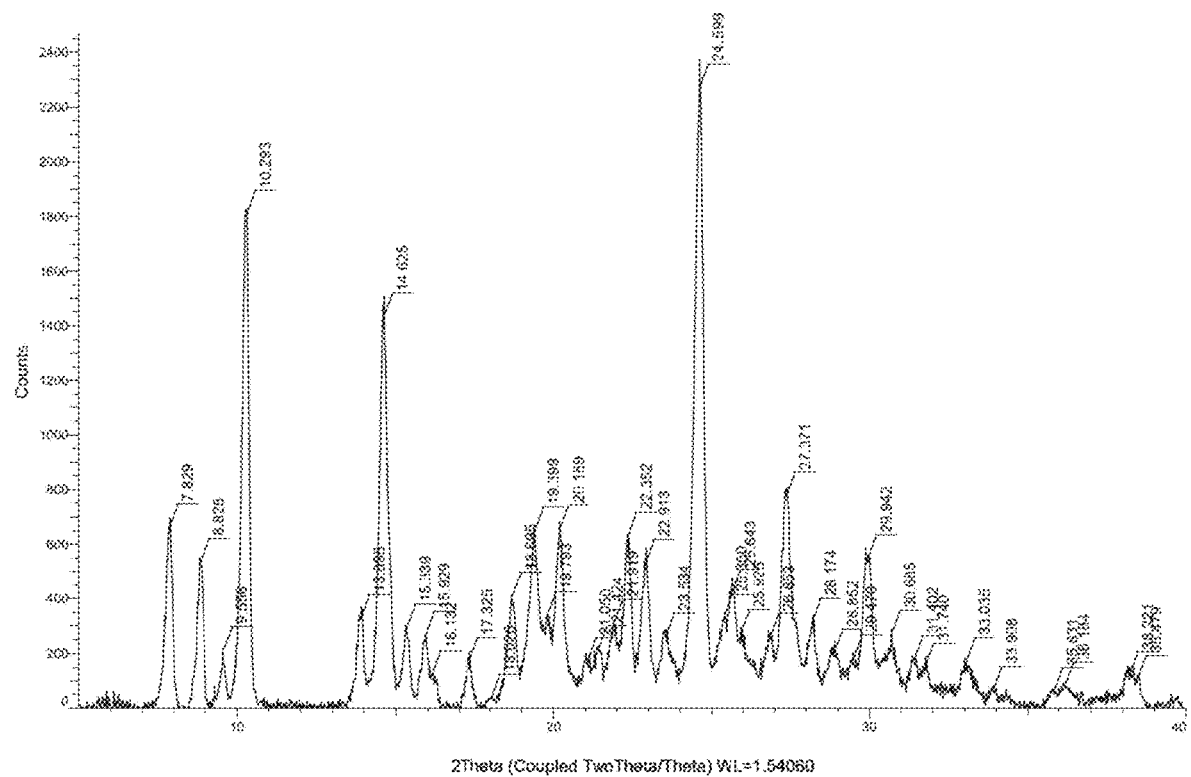
FIG. 1 is the XRD pattern of the crystal according to Example 1.

Example 1. Preparation of Crystalline Powder of Compound of Formula II 1.17 kg of the compound of formula II was sequentially slurried with 7.0 kg of ethyl acetate and 6.3 kg of anhydrous ethanol, each for 1 hour. The mixture was centrifugally filtered for more than 30 minutes until no liquid flowed out before the filter cake was dried at 25 to 35° C. in a water bath under reduced pressure in a vacuum oven with a vacuum degree of −0.10 to 0.06 MPa. The loss on drying was determined at 24 hours, which was ≤1.5%, and the crystalline powder of the compound of formula II was acquired. The X-ray powder diffraction (XRD) pattern given by Cu-Kα radiation is shown in FIG. 1.

Example 2. Determination of Solubility of Compound of Formula II 14.16 mg of the crystalline powder of the compound of the formula II acquired in Example 1 was dissolved, shaken overnight (24 hours) on a shaker at 37° C. and cooled to room temperature. The saturation concentration was measured using the supernatant. As a result, the saturation concentrations in the phosphoric acid solutions at pH 6.8 and 7.0 for 24 hours were 0.8 and 0.3 μg/mL, respectively. The compound was classified as a drug with low solubility according to the Biopharmaceutical Classification System (BCS).

Example 3. Measurement of Particle-Size Distribution, Specific Surface Area, and Dissolution Properties after Treatment with Different Pulverization Methods The crystalline powder of the compound of formula II acquired in Example 1 was mechanically pulverized (30 Hz, 80 mesh) and mixed in a hopper mixer (50 Hz, 3 to 20 rpm) to give sample powder 1.

The crystalline powder of the compound of formula II acquired in Example 1 was subjected to jet milling (0.2 to 4 bar) and hopper mixing to give sample powder 2.

The sample powders 1 and 2 were measured for the particle-size distribution and the specific surface area of particles of different particle size, and the results are shown in Table 2 below:

TABLE 2

Measurements of particle-size distribution and specific surface area of powders 1 and 2

| Sample | $X_{50}$ (μm) | $X_{90}$ (μm) | A (m$^2$/g) |
|---|---|---|---|
| Powder 1 | 3.96 | 64.89 | 11.09 ± 0.04 |
| Powder 2 | 2.66 | 14.01 | 13.07 ± 0.05 |

Figure 2:
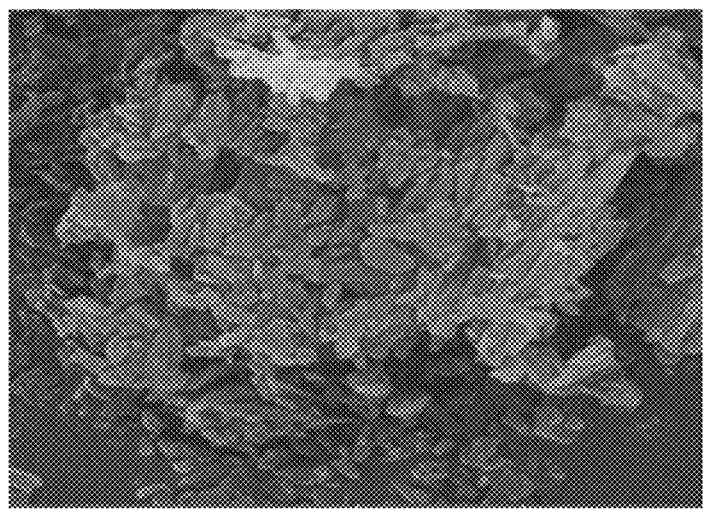
FIG. 2 is the crystal morphology of powder 1 from scanning electron microscopy.
Figure 3:
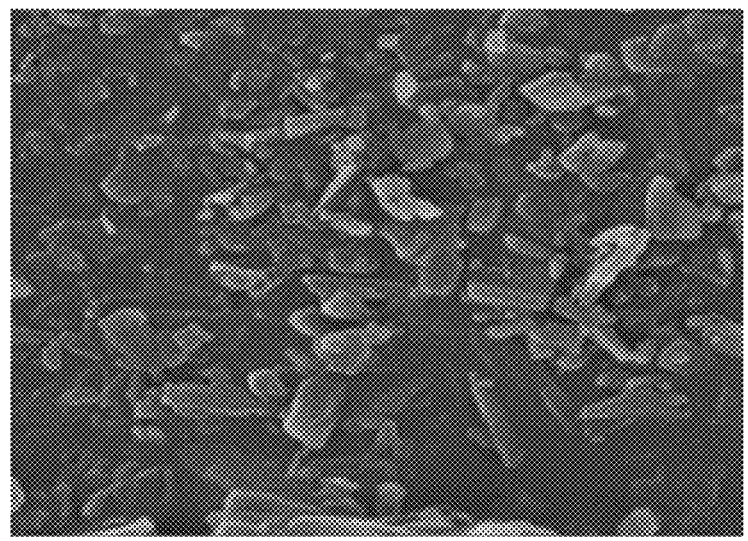
FIG. 3 is the crystal morphology of powder 2 from scanning electron microscopy.

The results show that: although the particle-size distributions of the two samples are significantly different, the specific surface areas of the two samples are similar; by scanning electron microscopy it was found that this was caused by the flaky crystal habit (powder 1 was an aggregated flaky crystal, and powder 2 was a thin flaky crystal) of the powders 1 and 2 (as shown in FIG. 2 and FIG. 3, respectively).

The dissolution properties of powders 1 and 2 in 1000 mL of 0.1 mol/L aqueous hydrochloric acid solution and a standard medium of 10 mM phosphate buffer containing 0.075% SDS, pH 6.8 were measured by basket method at 100 rpm and compared. The results are shown in Table 3 below:

TABLE 3

Measurements of dissolution properties of powders 1 and 2

| Sample | Time point | Cumulative dissolution % (0.1 mol/L hydrochloric acid) | Cumulative dissolution % (10 mM phosphate buffer containing 0.075% SDS, pH 6.8) |
|---|---|---|---|
| Powder 1 | 3 min | 89.6 | 77.4 |
|  | 5 min | 94.2 | 90.2 |
| Powder 2 | 3 min | 93.7 | 80.1 |
|  | 5 min | 95.8 | 86.4 |

The results show that: although the particle-size distributions of the two samples are significantly different, both samples exhibit the characteristics of rapid dissolution, i.e., the dissolution rate of the crystalline powder is about 90% at 5 minutes in 0.1 mol/L hydrochloric acid and a standard medium of 10 mM phosphate buffer containing 0.075% SDS, pH 6.8 by the basket method; and the dissolution properties of the two samples with different particle-size distributions have no significant difference.

Example 4. Measurement of Homogeneity and Dissolution Properties of Capsules Containing Compound of Formula II Six batches of capsules of the compound of formula II with strengths 8 mg/capsule, 10 mg/capsule and 12 mg/capsule were prepared from powder 1 in Example 3 according to the formulation in Table 4 (12 mg/capsule strength for example) and the conventional preparation methods in the art.

TABLE 4

Formulation of capsule of compound of formula II (12 mg/capsule, for 1000 capsules)

| Item | Amount |
|---|---|
| Compound of formula 11 (equivalent to 12.0 g of the compound of formula 1) | 14.16 g (5.7%) |
| Mannitol | 89 g (35.8%) |
| Microcrystalline cellulose | 138.4 g (55.7%) |
| Low-substituted hydroxypropyl cellulose | 5.9 g (2.4%) |
| Magnesium stearate | 0.99 g (0.4%) |

According to the content homogeneity inspection method of Chapter 0941 in Chinese Pharmacopoeia (Volume IV, 2015 Edition), the content homogeneity (A+2.2S) of the powders of capsules in different batches and different strengths was measured. As shown in Table 5, the A+2.2S were all less than 20, and the homogeneity of the capsule conforms to the regulation.

TABLE 5

Content homogeneity of compound of formula II in capsules

| Number | Strength | A + 2.2 S |
|---|---|---|
| 1 | 8 mg | 5.5 |
| 2 |  | 5.4 |
| 3 | 10 mg | 8.0 |
| 4 |  | 7.4 |
| 5 | 12 mg | 6.8 |
| 6 |  | 10.4 |

According to the content homogeneity inspection method of Chapter 0931 in Chinese Pharmacopoeia (Volume IV, 2015 Edition), samples 5 and 6 were dissolved in 1000 mL of 0.1 mol/L aqueous hydrochloric acid solution as a medium at 100 rpm. An appropriate amount was taken at 5 min, 10 min, 20 min, 30 min, 45 min and 60 min, filtered, supplemented with the same amount of medium and filtered again. The latter filtrate was measured for the cumulative dissolution in the medium. The results are shown in Table 6.

TABLE 6

Dissolution properties of the compound of formula
II in capsules in 0.1 mol/L hydrochloric acid

| Dissolution (%) Time (min) | Number | |
|---|---|---|
| | 5 | 6 |
| 5 | 97.4 | 96.3 |
| 10 | 100.1 | 98.5 |
| 20 | 100.3 | 99.3 |
| 30 | 99.9 | 99.2 |
| 45 | 101.1 | 98.4 |
| 60 | 99.3 | 100.1 |

What is claimed is:

1. A crystalline powder of the compound of formula II, comprising crystals exhibiting a thin flaky or an aggregated flaky habit, the crystalline powder comprising a specific surface area ≥10 m$^2$/g and a particle-size distribution of $X_{50}$≤50 μm and/or $X_{90}$≤500 μm, Formula II ·2HCl wherein, in an X-ray diffraction (XRD) pattern using Cu-Kα radiation, the crystals have diffraction peaks at the following 2θ of 7.83±0.2°, 8.83±0.2°, 10.29±0.2°, 14.63±0.2°, 24.60±0.2° and 27.37±0.2°.

2. The crystalline powder according to claim 1, wherein the crystalline powder comprises a specific surface area of 10 to 50 m$^2$/g.

3. The crystalline powder according to claim 2, wherein the crystalline powder comprises a specific surface area of 10 to 25 m$^2$/g.

4. The crystalline powder according to claim 2, wherein the crystalline powder comprises a specific surface area of 10 to 15 m$^2$/g.

5. The crystalline powder according to claim 1, wherein the particle-size distribution of the crystalline powder is 20 μm≤$X_{50}$≤50 μm and/or 300 μm≤$X_{90}$≤500 μm.

6. The crystalline powder according to claim 1, prepared by a method comprising:
(1) slurrying the compound of formula II with one or more organic solvents selected from ethanol, ethyl acetate, methanol, and acetone by stirring, mixing and separating until no liquid flows out, thereby preparing a mixture;
(2) heating and drying the mixture under reduced pressure; and
(3) optionally, pulverizing and mixing,
thereby preparing the crystalline powder.

7. The crystalline powder according to claim 1, wherein, in the X-ray diffraction (XRD) pattern using Cu-Kα radiation, the crystals additionally have diffraction peaks at the following 2Θ 9.56±0.2°, 13.90±0.2°, 19.40±0.2°, 20.19±0.2°, 22.35±0.2° and 22.91±0.2°.

8. The crystalline powder according to claim 1, wherein, in the X-ray diffraction (XRD) pattern using Cu-Kα radiation, the crystals additionally have diffraction peaks at the following 2Θ 9.56±0.2°, 13.90±0.2°, 15.34±0.2°, 15.93±0.2°, 17.32±0.2°, 18.70±0.2°, 19.40±0.2°, 20.19±0.2°, 22.35±0.2°, 22.91±0.2°, 25.64±0.2°, 28.17±0.2° and 29.94±0.2°.

9. The crystalline powder according to claim 1, wherein, in the X-ray diffraction (XRD) pattern using Cu-Kα radiation, the crystals have an XRD pattern essentially identical to FIG. 1.

10. The crystalline powder according to claim 1, wherein the particle-size distribution of the crystalline powder is $X_{50}$≤20 μm and/or 150 μm≤$X_{90}$≤300 μm.

11. The crystalline powder according to claim 1, wherein the particle-size distribution of the crystalline powder is $X_{50}$≤10 μm and/or 70 μm≤$X_{90}$≤150 μm.

12. A crystalline powder composition, comprising the crystalline powder according to claim 1 in an amount that accounts for 70 wt % or more by weight of the crystalline powder composition.

13. A crystalline powder composition, comprising the crystalline powder according to claim 1 in an amount that accounts for 50 wt % or more by weight of the crystalline powder composition.

14. A pharmaceutical composition, comprising the crystalline powder composition according to claim 13, and one or more pharmaceutically acceptable carriers.

15. A pharmaceutical composition, comprising the crystalline powder according to claim 1, and one or more pharmaceutically acceptable carriers.

16. A method for treating non-small cell lung cancer, comprising administering to a patient in need thereof a therapeutically effective amount of the pharmaceutical composition according to claim 15.

17. A method for preparing the crystalline powder according to claim 1, the method comprising:
(1) slurrying the compound of formula II with one or more organic solvents selected from ethanol, ethyl acetate, methanol, and acetone by stirring, mixing and separating until no liquid flows out thereby preparing a mixture;
(2) heating and drying the mixture under reduced pressure; and
(3) optionally, pulverizing and mixing,
thereby preparing the crystalline powder.

18. The method for preparation according to claim 17, wherein the one or more organic solvents are selected from ethanol, ethyl acetate, and a mixture of ethanol and ethyl acetate.

* * * * *